United States Patent [19]

Saito et al.

[11] 4,019,864

[45] Apr. 26, 1977

[54] METHOD FOR MEASURING RADIOACTIVITIES OF TRITIUM AND CARBON-14 IN SAMPLE AIR AND APPARATUS FOR PERFORMING THE SAME METHOD

[75] Inventors: Tomo Saito, Sagamihara; Kazuo Watanabe, Yokohama; Yumiko Nishiyama, Hatano; Naotake Morikawa, Tokyo, all of Japan

[73] Assignee: Sagami Chemical Research Center, Tokyo, Japan

[22] Filed: Sept. 10, 1975

[21] Appl. No.: 611,958

[30] Foreign Application Priority Data

Sept. 10, 1974 Japan .................... 49-104215
Apr. 10, 1975 Japan .................... 50-48522[U]
Apr. 10, 1975 Japan .................... 50-43624

[52] U.S. Cl. .................... 23/253 PC; 250/303
[51] Int. Cl.² .................... G01N 31/12; G01T 1/167
[58] Field of Search ..... 23/232 R, 230 PC, 253 PC, 23/230.3, 232 E; 250/303, 304, 364

[56] References Cited

UNITED STATES PATENTS

| | | | |
|---|---|---|---|
| 3,050,372 | 8/1962 | Scott | 23/232 R X |
| 3,682,598 | 8/1972 | Kaartwen | 23/253 PC X |
| 3,811,838 | 5/1974 | Saito et al. | 23/232 R X |
| 3,832,137 | 8/1974 | Mlinko et al. | 23/230.3 |

OTHER PUBLICATIONS

Bosshart et al., Anal. Chem. 44, 1117(1972).
Scott et al., Anal. Chem. 38, 1404(1966).

*Primary Examiner*—Robert M. Reese
*Attorney, Agent, or Firm*—Sughrue, Rothwell, Mion, Zinn & Macpeak

[57] ABSTRACT

An air sample including substances containing tritium and substances containing carbon-14 is oxidized continuously while measuring a volume thereof and water and carbon dioxide included in the oxidized air sample are collected respectively continuously. After water and carbon dioxide are recovered, the radioactivities thereof are measured respectively.

4 Claims, 12 Drawing Figures

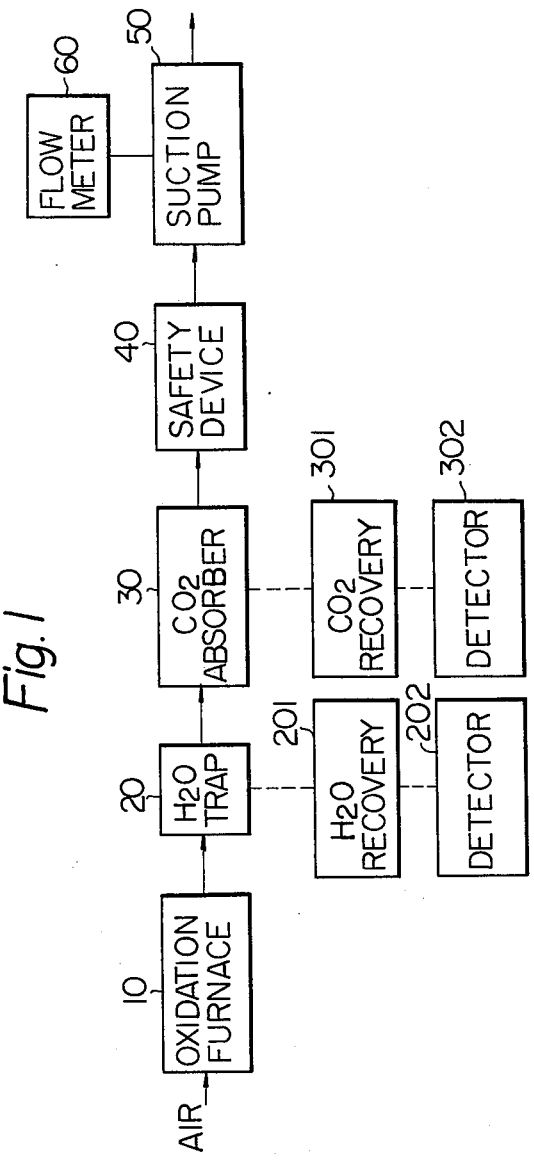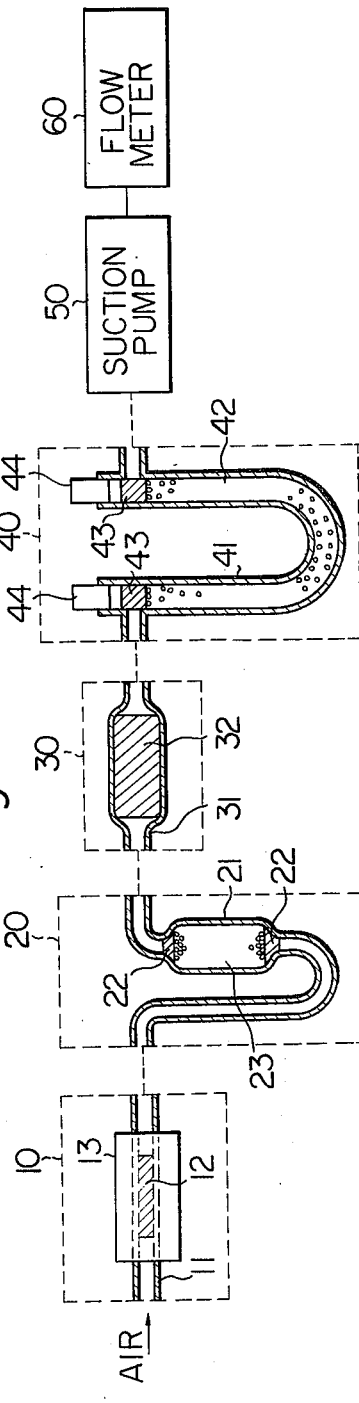

METHOD FOR MEASURING RADIOACTIVITIES OF TRITIUM AND CARBON-14 IN SAMPLE AIR AND APPARATUS FOR PERFORMING THE SAME METHOD

BACKGROUND OF THE INVENTION

1. Field of the Invention

The present invention relates to a method for measuring tritium and carbon-14 contained in an air sample and an apparatus for performing the same method.

2. Description of the Prior Art

Tritium and carbon-14 contained in air may, in general, exist in various chemical structures and, therefore, in order to measure the amount of each nuclide precisely, it is convenient to integrate these chemical shapes by using a suitable chemical processing.

As a monitor of $^3H$ and $^{14}C$ contained in air, an ionization chamber has been used widely. This is because it is possible to fabricate an ionization chamber having a large volume in comparison with radioactive detectors of other known type. That is, where there is a large amount of sample having low specific radioactivity, i.e., for example, where air is contaminated with a relatively small amount of radioactive substances, it is necessary to collect a large volume of contaminated air in a detector having large volume to measure the radioactivity of the pollutant. For this reason, an ionization chamber whose volume is generally 5–15 liters has been used heretofore as an ordinary environment monitor. However, in the radioactive measurement using ionization chamber, where water and/or other substances, which would degrade the electrical insulation of the chamber, co-exists in air, the measurement itself become very difficult and it is hardly to expect a precise radioactive measurement. To this end, sample is sufficiently dried by using desiccating agent such as silica gel etc. and then introduced into an ionization chamber, or a filter suitable to neutralize ions in air is used. Therefore, there is no problem in a case where the radioactive substances included in the sample has chemical structure which can not be collected by the silica gel etc. used in the preceding stage. However, in a case where the radioactive substances have structures which possibly be collected by the silica gel etc., the measured radioactive value will become unreasonably low. That is, a negative error will be introduced. By considering, particularly, the facts that most of tritium existing in environment takes the form of water and that, where a volatile, labelled compounds are exhausted from an installation in which radioactive substances are handles, the compounds may easily be adsorbed irreversibly by silica gel etc., it can be said that the conventional ionization chamber type monitor was unacceptable. Further, with the ionization chamber type monitor, erroneous radioactive measurement due to smokes etc. is performed resulting in a positive error.

In another method for monitoring tritium in air, which has been recently developed, the water content in air is absorbed by silica gel etc., and then the radioactivity thereof is measured by the liquid scintillation counting method. The method improves the ionization chamber monitor partially. However, the method wherein the water content in air is collected by a desiccating agent such as silica gel etc. and the radioactivity thereof is measured (hereinafter, referred to as condensation method) is based on the general assumption that the object to be measured is in the form of water almost completely. However, since substances other than water, for example, most of organic substances, would be adsorbed at normal temperature, a positive error will be produced if the radioactivity of water is measured by the condensation method, and it can be considered that all tritium in air is measured. This is because a monitoring for substances which will pass through silica gel without absorption is theoretically impossible.

On the other hand, in a case where the ionization chamber method and the condensation method are merely combined, it is possible for radioactivities of $^3H$, $^{14}C$ as a whole to obtain a better result than that obtainable by using these two methods individually. However, the information obtainable from the combination of the two methods is essentially a sum of the radioactivities, and as informations about the amount of radioactivity for each of nuclides $^3H$ and $^{14}C$ can not be provided at all. This is because, it is impossible to distinct between $^3H$ and $^{14}C$ in the ionization chamber system. Furthermore, in the case of the combination of the conventional methods, if other radioactive substances than $^3H$ and $^{14}C$ are contained in a sample, the total radioactivity of the other substances will be added to those of $^3H$ and $^{14}C$, resulting in a positive error for the measurement of $^3H$ and $^{14}C$.

SUMMARY OF THE INVENTION

An object of the present invention is to provide a method of radioactive measurement in which mutually disturbing radioactive substances are separately collected whereby tritium and carbon 14 contained in air can be measured without error.

Another object of the present invention is to provide an apparatus for performing the method.

Another object of the present invention is to provide an improved carbon dioxide collecting device which is particularly useful with a highly viscous collecting agent.

A further object of the present invention is to provide an apparatus useful to analyze a metabolism of medicines labelled with tritium and/or carbon-14 and given to a small size animal by collecting water and/or carbon dioxide in the respiration of the animal and measuring the radioactivities of the water and carbon dioxide.

A still further object of the present invention is to provide an apparatus which can operate to continuously collect $H_2O$ and/or $CO_2$.

The above objects of the present invention are achieved, according to the present invention, by oxidizing an air sample to convert substances containing tritium and/or carbon-14 into tritium water and 14-carbon dioxide, collecting tritium water and/or 14-carbon dioxide individually and measuring radioactivities thereof respectively. In collecting tritium water and 14-carbon dioxide, a cold trap and a monoethanol amine carbon dioxide absorber are preferably used respectively.

The air sample is introduced into an oxidation furnace by which the air sample is converted into water and carbon dioxide and then conducted into the cold-trap by which water is collected. The remaining portion is then introduced into a carbon dioxide collecting device which has a unique construction and is filled with monoethanol amine without diluent. After carbon dioxide component is removed by the carbon dioxide absorber, the remaining portion is discharged through a safety device, if necessary. The water and carbon dioxide collected by the respective collecting devices are recovered suitably and the radioactivities thereof are measured by the liquid scintillation counting method. In order to obtain data concerning time variations of amounts of label nuclides, a plurality of series connections each including the cold-trap and the carbon dioxide absorber are arranged in parallel together with suitable valve means so that these series connections are selectively opened to pass the sample gas through only one of them in one of a series of time intervals by sequentially controlling the valve means. The latter means system is extremely useful in analizing metabolism of medicines in animal body.

BRIEF DESCRIPTION OF THE DRAWING

FIG. 1 is a block diagram of an embodiment of the apparatus suitable to perform the method of the present invention;

FIG. 2 is the same as FIG. 1, showing some details thereof;

DESCRIPTION OF THE EMBODIMENTS

Figure 3:
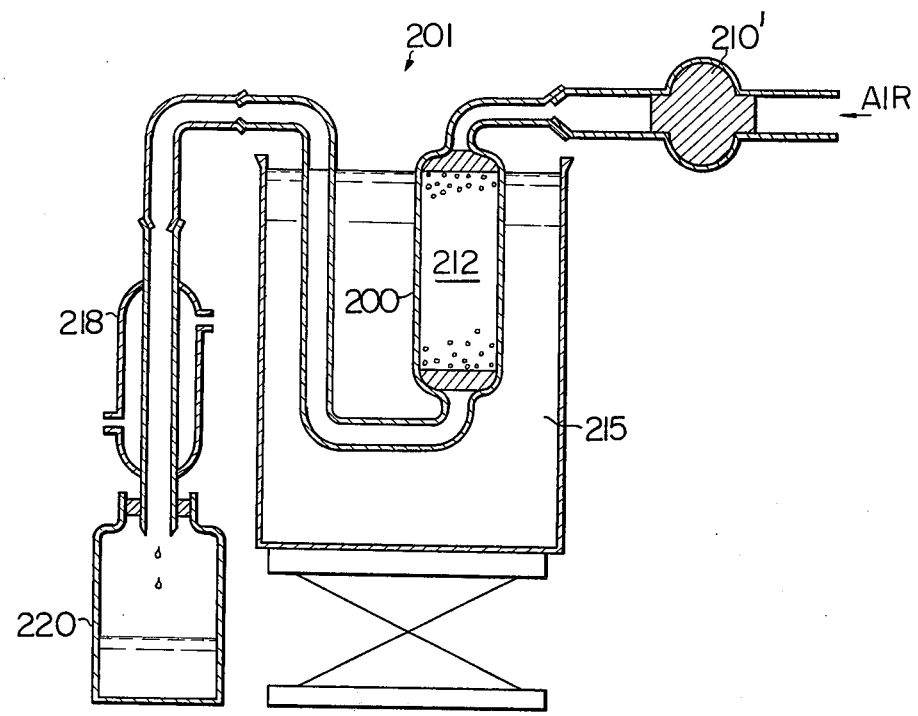
FIGS. 3 and 4 show examples of the water recovery device useful in the apparatus in FIG. 1.

FIG. 1 is a block diagram of an embodiment of the apparatus suitable for performing the method of the present invention.

Describing this apparatus along with a passage of gas flow, it comprises a sample oxidizing section 10, and $H_2O$ adsorbing section 20, a $CO_2$ adsorbing section 30, a safety device 40, a sample gas suction pump 50, a gas flow meter 60 for measuring a whole volume of the passed sample, a means 201 for recovering tritium water adsorbed by the $H_2O$ adsorbing section 20, a recovering means 301 for carbon dioxide collected in the $CO_2$ collecting section 30 and means 202 and 203 for detecting the radioactivities of the recovered water and carbon dioxide, respectively. That is, a sample gas is suctioned by the suction pump 50 into the sample oxidizing section 1 in which the sample is oxidized to convert compounds containing hydrogen into water and compounds containing carbon into carbon dioxide. Then water, carbon dioxide and other components such as nitrogen are passed through the $H_2O$ absorbing section 20 by which water is captured.

The remaining carbon dioxide and other components are passed through the $CO_2$ absorbing section by which only carbon dioxide is captured. The remainder is introduced, if necessary, into the safety device 40 and absorbed thereby to prevent unaimed radioactivity which would possibly contained therein from being discharged.

The flow meter 60 for measuring the whole volume of the gas passing through the above mentioned path is connected to the suction pump.

FIG. 2 shows a practical example of the air sample flowing system of the apparatus in FIG. 1. The sample oxidizing section 10 comprises a burning tube 11 of quartz, porcelain or other heat resistive metal and housing a catalyst 12 of cuprous oxide, platinum or palladium carried on a suitable carrier such as asbestos or silica gel etc. and an electric furnace 13 surrounding the burning tube 11. The thickness and length of the burning tube 11 are determined by the suction velocity of the sample air given by the suction pump 50. For example, when the apparatus is operated with the suction velocity in the order of 1 lit./minute, it has been found that the thickness, i.e., diameter in the order of 1.5 cm and the length in the order of 20 cm. are suitable.

The temperature of the electric furnace 13 is 600° C or higher and it may be desirable to select it as 800°–850° C.

The $H_2O$ absorption section 20 includes a desiccating agent 23 such as, for example, silica gel, anhydron etc. which is supported in place by quartz fiber 22. Although silica gel etc. may be used simply, absorption and/or removal of $H_2O$ with respect to such agent is not always quantitatively performed. That is, even if the amount of water collected is quantitative, the radiochemical yield is not always quantitative. Therefore it may be advisable to utilize a cold-trap for this purpose. In a case where the cold-trap is employed, icy water or dry-ice may be used as cooling agent.

The $CO_2$ absorption section 30 is used to collectively absorb $CO_2$ from a mixture of $CO_2$ and other components passed through the $H_2O$ absorption section 20 and it may use, as a fixing agent 32, organic amines such as monoethanol amine, hyamine etc., caustic alkali or barium chloride under basic condition. Where the radioactive measurement is performed by using liquid scintillation counting method, ethanol amine will be most convenient. Since monoethanol amine is a viscous liquid, it is impregnated into thin quartz cotton or absorbent cotton etc. and the monoethanol amine impregnated cotton fills the tube 31. The shape of the tube 31 is linear and the size thereof is determined by the volume of gas to be passed therethrough. For example, where the volume of the passing gas is in the order of 1 lit./minute, a good result has been obtained when the inner diameter and the length of the tube 31 are selected as 1 cm and 12 cm, respectively.

Among the gas output from such sample oxidization section, the remaining portion thereof which does not include $H_2O$ and $CO_2$ is introduced into the safety device 40. The safety device 40 comprises a U-shaped tube 41 and, in the U-shaped tube, activated carbon 42 fills. The reference numeral 43 is a member for preventing the activated carbon from leaking out and 44 is a stopper of suitable material. The purpose of this safety device 40 is to absorb radioactive nuclides other than $^3H$ and $^{14}C$, which may possibly be contained in air, so that these other nuclides are prevented from being discharged into air as they are.

The volume of air introduced by the suction pump 50 into this system is measured by the gas meter 60 connected to the pump 50. It is convenient to use an integral type meter as the gas meter 60 and the integral type gas meter will provide a precise measurement. That is, since the respective absorbing sections (20, 30, 40) in this system provide not always constant resistivities against the gas flow, the use of an ordinary flowmeter for measuring the whole volume will provide an increasing error. Therefore, by the use of integral type gas meter, such error resulting from the resistivity variation may be eliminated.

Next, the present method using the above mentioned apparatus will be described in which silica gel and monoethanol amine impregnated cotton are used for convenience. The sample air is suctioned by the suction pump 50 into the sample oxidizing portion 10. The sample firstly passes through the catalyst 12 in the quartz tube 11 heated by the electric furnace 13 and is oxidized therein. $H_2O$, $^3H_2O$, $CO_2$ and $^{14}CO_2$ in the sample are directly passed and other organic substances are converted into $H_2O$, $^3H_2O$, $CO_2$ and $^{14}CO_2$ by the oxidization. The sample containing converted substances inclusively are immediately introduced into the $H_2O$ absorbing agent 23, such as silica gel, contained in the tube 21 where $H_2O$ and $^3H_2O$ in the sample are collected. The sample dehydrated in this manner is subsequently introduced into the $CO_2$ absorbing portion 30 where $CO_2$ and $^{14}CO_2$ are collected by, for example, monoethanol amine 32.

The portion of the sample exclusive of water and carbon dioxide is passed through the activated carbon 42 in the safety device 40 to absorb other radioactive gas components to thereby eliminate the possible interference due to the radioactive substances.

During this, the volume of the air sample introduced by the suction pump 50 into this apparatus is integrally measured by the meter 60.

The water component absorbed by the desiccating agent in the $H_2O$ absorbing portion 20 is recovered by a water recovering device 201.

Figure 4:
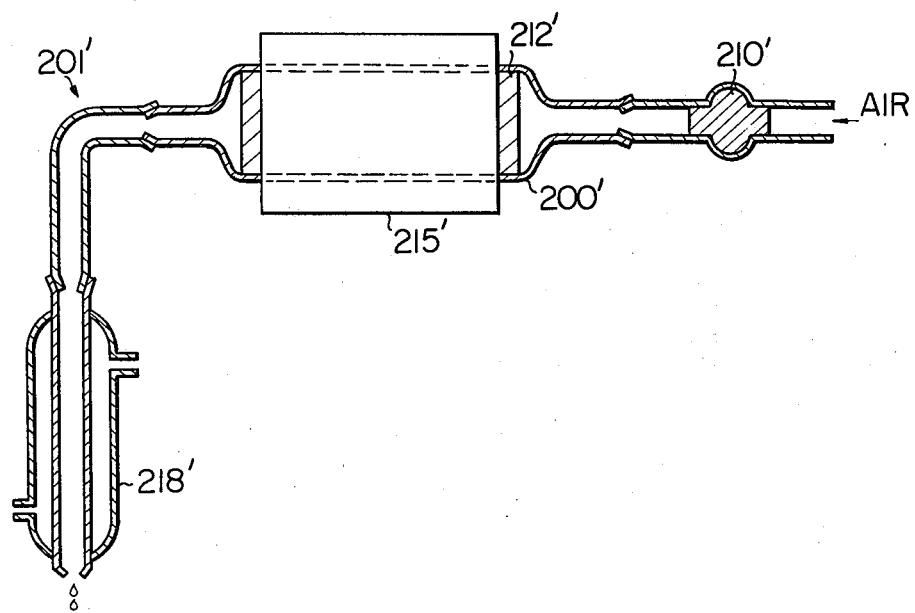

FIG. 3 and FIG. 4 are examples of the water recovery device 201, respectively. In FIG. 3, the tube 200 is immersed in an oil bath 215 and in FIG. 4 a tube 200' is heated by using an electric heater 215', to maintain the temperature of the tube 200 or 200' at 150°–180° C and simultaneously a pressurized air is supplied to the desiccating agent 210' to thereby discharge quantitatively the water absorbed in the tube 200 or 200' as steam. This discharged steam is liquified by a cold-trap 218 or Liebig condenser 218' etc. The liquefied water is recovered by a measurement vial 220 for liquid scintillation counter device 202 and scintillation-counted after adding a suitable amount of scintillator to the water to measure the radioactivity. On the other hand, where tritium water is collected by the use of the cold-trap, it is collected in the similar manner by provision and removal of the heating device or washing out from the cold-trap and measured in the similar manner by the scintillation counting method or other measuring method.

As a typical example of the water absorbing portion 20 used herein, a glass tube having length 12 cm and diameter 1.5 cm as the tube 21 filled with an amount of drying silica gel of 40–80 mesh, the collection efficiency of substantially 100% is obtained for about 5 gm. water at normal temperature with gas flow rate in the order of 1 lit./minute. In addition, the shape of the tube may be U shape where the water is to be recovered by the bath as mentioned previously or a linear type one where the electric heating device is used. However, as mentioned previously, the cold-trap is highly desirable for water collection.

There is a case where the collection of carbon dioxide in the $CO_2$ absorbing section 30 may not always become 100% dependent on the filling condition of the collecting agent 32 in the absorbing tube 31 and a variation of the air flowing condition. In this case, it may be possible to add another tube similar to the absorption tube 31 and being filled with anhydrous magnesium perchlorate to thereby calculate the carbon dioxide collecting efficiency precisely by comparing with the increment of the weight.

14-carbon dioxide collected by the carbon dioxide collecting agent is measured on radioactivity by means of the liquid scintillation counting method or other method.

In the present invention, although it is possible to use silica gel, anhydron, potassium chloride, sodium sulfate etc. as the water absorbing agent in the water absorbing portion 20, it has been found that desiccants such as potassium chloride, sodium sulfate etc. are not adequate because of their relatively low water-absorbing velocity. Although the collecting agent of the carbon dioxide absorbing portion, materials other than the above mentioned ones, such as sodium hydroxide, potassium hydroxide etc., also be considered, they are not suitable because the subsequent radioactive measurement will become complicated.

Figure 5:
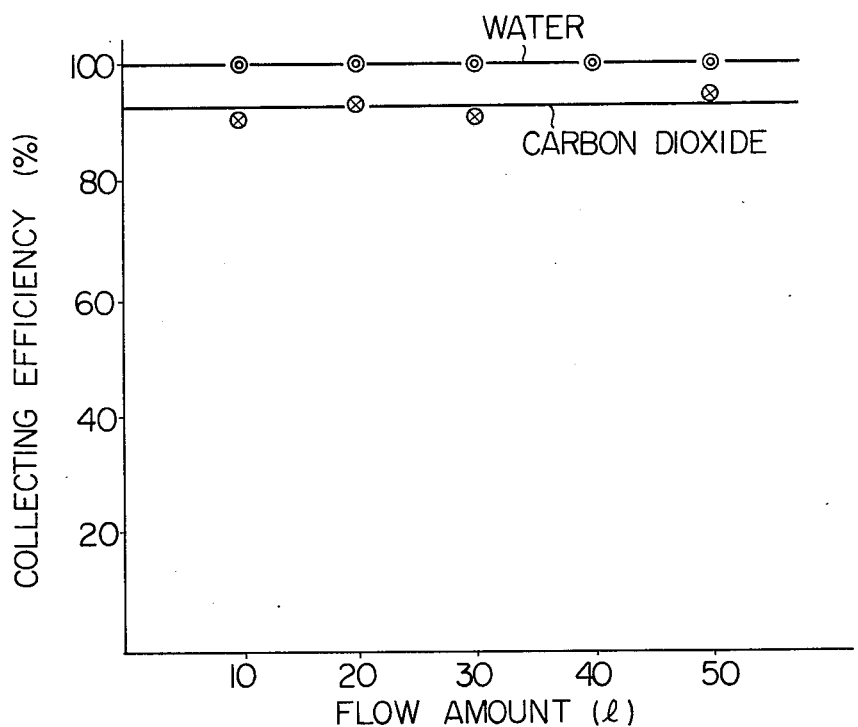
FIG. 5 shows an example of the collecting efficiency of water and carbon dioxide with using the weight method.

FIG. 5 shows an example of measurement of the collecting efficiencies of $H_2O$ and $CO_2$ in air, which are collected by silica gel and the monoethanol amine impregnated cotton, respectively, by using the weight method. The temperature and flowing velocity during the measurement were 28° and 40 lit./hour respectively. As the water absorbing tube 20, a glass tube of 15 mm diameter and 12 cm length was used with the filling of 40–80 mesh silica gel for drying. Further, as the carbon dioxide collecting tube, a glass tube of 10 mm diameter and of 12 mm length was used and an absorbing cotton impregnated with absorbed 1 cc of ethanol amine filled the interior of the glass tube. The upper plots in FIG. 5 shows the collecting efficiency for water and the lower plots shows the collecting efficiency for carbon dioxide. The average collecting efficiency for water is 99.8% and it is almost 100%. On the other hand, the efficiency for carbon dioxide is 92.4% and this is sufficient level to use practically.

In addition, as to the detection limit for $^{14}CO_2$ and $^3H_2O$, an identifiable limitation is about $1 \times 10^{-5}$–$1 \times 10^{-6}$ micro Curie/cm for, for example, tritium when detected by the ionization chamber method, while, in the present method, $0.9 \times 10^{-10}$ micro Curie/cm$^3$ can be monitored, resulting in an improvement in practical sensitivity by 4–5 orders. On the other hand, for $^{14}C$, $3.6 \times 10^{-10}$ micro Curie/cm$^3$, becomes possible to monitor according to the present invention.

According to the method of the present invention, those radioactive substances which possibly interfere the precise measurement can easily be chemically removed and thus such problem as interference of those substances becomes not a problem. In a case where radioactive nuclides such as $^{85}Kr$ etc. is included in the sample, positive errors for $^3H$ and $^{14}C$ monitoring are produced in the conventional method. According to the present method, since these nuclides are insensitive in any absorbing tubes, they become not problem.

Further, although in any of the conventional two method, a positive error with be produced in the measurement of $^3H$ and/or $^{14}C$, such error can reliably eliminated according to the present invention by using CuO as the oxidizing catalyst or using silver as one part of it.

Therefore, the present method is most suitable to determine precisely the amounts of respective $^3H$ and $^{14}C$ in the sample air.

As the performances required to monitor radioactive substances, one of them may be to detect all radioactivities existing therein, i.e., to determine the whole amount thereof. As other performances, it is required to determine what radioactive nuclides exist with how much amount of each.

This is because the biological poisonings thereof are much different depending on the respective nuclides. In view of this point, the utility of this invention is obvious in that the present method distinguishes between the nuclides, i.e., between tritium and carbon-14 and renders possible to precisely determine the amount of each nuclide.

As to the carbon dioxide collecting device, it is usual to use monoethanol amine as collecting agent for absorbing carbon dioxide in a gas sample by passing the sample through the agent and then to recover the absorbed carbon dioxide by washing out the monoethanol amine for subsequent radioactive measurement.

The structure of the carbon dioxide collecting device used in the previous embodiment is effective to absorb carbon dioxide. However, as to the washing out of the agent, such structure as mentioned is not convenient. In order to facilitate the washing out of the agent, it is convenient to use a jar filled with a sample of the absorbent and feed air to the bottom portion of the jar.

As well known, since monoethanol amine is highly viscous, bubbles produced during the passing-through of the gas sample in the jar are hardly sub-divided and thus the gas-liquid contact can not be increased sufficiently, resullting in a problem in view of absorption efficiency. In order to resolve this problem, it is usual to use a relatively thin and long tube filled with a sufficient amount of monoethanol amine so that the time for which bubbles of the sample gas can exist in the tube is sufficiently elongated or to reduce the viscosity of monoethanol amine by adding a diluent such as alcohol or water. The amount of alcohol solution of monoethanol amine required to absorb carbon dioxide by some satisfactory amount depends upon the diameter of tube, the velocity of gas and the size of bubbles. For collection of, for example, carbon dioxide contained in the respiration of a small size animal, the amount of the solution may be estimated generally as the order of, for example, 200 cc for 15% solution. However, since the volume of the absorbent solution is limited up to 0.5 cc for the liquid scintillation counting method, only about one-four hundredth of $^{14}CO_2$ absorbed is available for radioactive measurement.

Further, in this case, since the liquid available contains $^{14}CO_2$ as well as water, the solubility thereof into the liquid scintillator becomes about 0.5 ml./15 ml (scintillator). On the other hand, where monoethanol amine is used solely, the liquid available does not contain water content and the solubility becomes about 4 ml./15 ml. Therefore, if the sole use of monoethanol amine becomes possible, the amount of the medicines to be given will become one four hundreth or lesser to obtain the same counting rate as that obtainable by monoethanol amine-alcohol solution.

Furthermore, when monoethanol amine-alcohol solution is used, alcohol will be vaporized. Therefore, it is difficult to use an exhaust pump to make the respiration passing through, and, for this reason, an aspirator has been used to do so. However, it is common knowledge that the drain water for installation where radioactive substances are handled should be minimized for safety purpose and, in view of this point, the conventional device is insufficient.

Therefore, it is desired to provide a collection device adapted particularly to be used together with absorbent having high viscosity for absorbing components in gas, with which the washing out of the absorbent after completion of the absorption becomes very easy with high efficiency.

Figure 6:
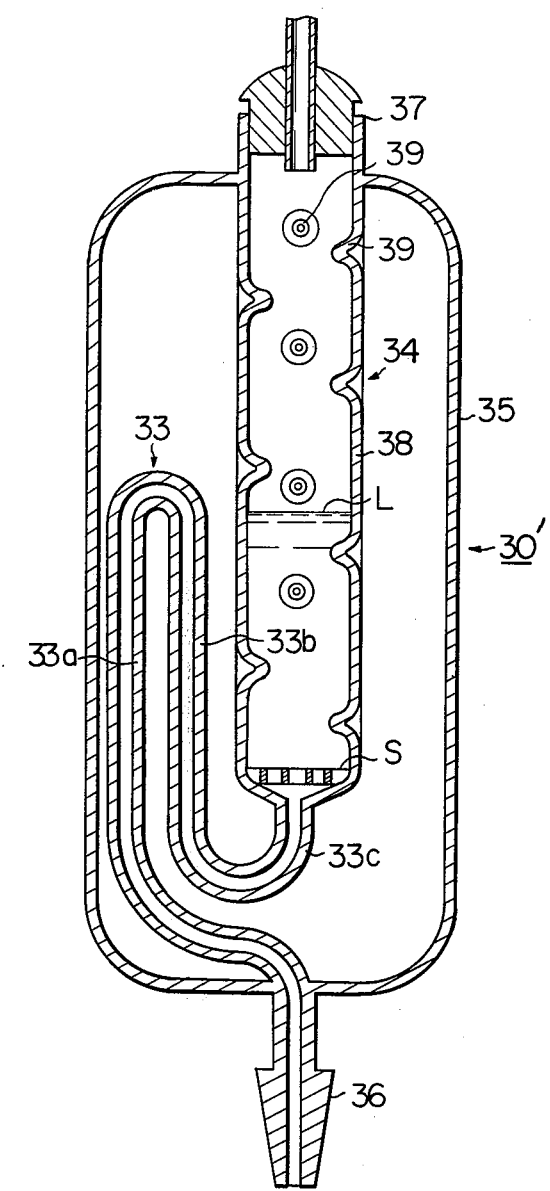
FIG. 6 is a cross section of an improved carbon dioxide collecting device according to the present invention.

FIG. 6 shows an embodiment of the $CO_2$ collecting device according to the present invention, in which a body 34 of an absorbing tube is defined substantially by a wall 38 as a cylinder, an inlet port of which is positioned at the lower end thereof and has a relatively narrow passage. Provided on an inner surface of the wall 38 of the body 34 are a plurality of protrusions 39 with suitable spaces. The end of the gas inlet is directly connected to an end 33c of one leg portion 33b of a reverse U shape syphon portion 33, the other leg portion 33a of which is connected to a gas inlet 36. The syphon portion 33 and the body portion 34 may be formed separately and jointed thereafter or may be formed as a single piece as shown in the drawing. In the latter case, it is preferable to support the syphon portion 33 and the body portion 34 by means of an outer wall or shell 35 provided between the inlet port 36 and an outlet port 37 of the body portion 34 and protected thereby.

A highly viscous liquid is inserted from the outlet port 37 up to a level such as shown by letter L. In this condition, when a gas is supplied from the inlet 36, the gas passes through the syphon portion 33 and enters into the interior of the body in which it becomes bubbles which continue to move upwardly as they are and the ability of the absorbent for a desired component of the gas in the form of bubbles is not sufficient. In the apparatus of the present invention, the gas entering from the lower end 33c as bubbles is subdivided by the protrusions 39 and when the bubbles reach around the level surface, these are broken up by the protrusions 39 whereby the gas-liquid contact efficiency is increased as the whole and thus the absorption is facilitated.

According to experiments, it has been found that, in comparison with the conventional method where a simple collecting tube is filled with monoethanol amine and gas is supplied from the lower end thereof, the amount of monoethanol amine when the apparatus of the present invention is employed becomes at least the order of one-tenth for absorbing a sufficient amount of carbon dioxide and it is sufficient to use about one-thirtieth to one-fortieth as the case may be.

Description next the function of the syphon portion 33, the portion 33a firstly facilitates the supplying or feeding of gas to the lower portion 33c of the body portion. That is, in the conventional method, a relatively large volume container is filled with monoethanol amine alcohol solution and a gas is fed through a tube having lower end open into the container through which the gas moves upwardly as bubbles. The portion 33a of the syphon portion 33 according to the present invention functions in the same manner as the open ended tube. The reason for why this portion is constituted as syphon structure is to facilitate the washing out of monoethanol amine which has absorbed, for example, carbon dioxide. According to the syphon structure of the present invention, it is possible to remarkably simplify the process up to the washing-out. That is, after the completion of absorption, monoethanol amine is washed sufficiency by adding a suitable washing-out agent (in this case, alcohol) from the outlet port of the main body portion 34 until it fills the syphon portion up the top level thereof and thereafter an additional volume of alcohol is added so that the sufficiently washed monoethanol amine is immediately flown out from the inlet port 36 through the syphon portion 33. Accordingly, the measuring method such as liquid scintillation counting is immediately employed without needs of preparation of the complicated apparatus and operation thereof.

In addition, since the concentration of carbon dioxide absorbed by monoethanol amine becomes about 40 times that obtainable by using the conventional method, the fidelity of the counting measurement becomes very high.

Further, a member S such as shown in FIG. 6 which is suitable to facilitate the subdivision of the bubbles may be used in the bottom portion of the upstanding body portion, if necessary. The member S may be in the form of a mesh of suitable filaments, a lattice of any suitable material as shown or the like. In the case shown, however, the member S should not be obstruction to the washing out process.

Figure 7:
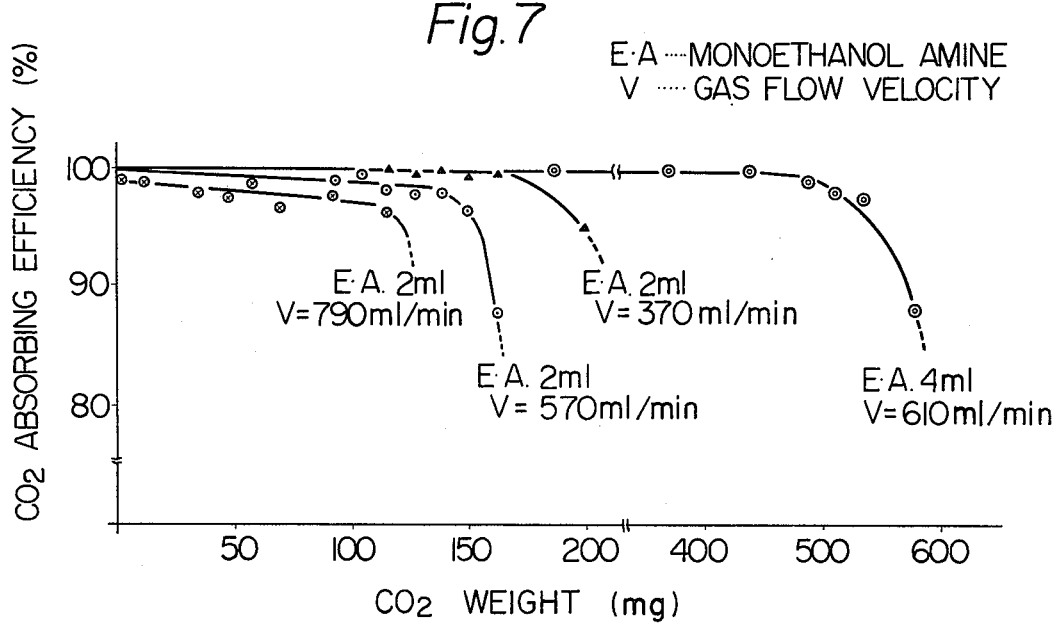
FIG. 7 shows a graph showing the collecting efficiency of carbon dioxide when a carbon dioxide absorber according to the present invention is used.

FIG. 7 is a graph showing the carbon dioxide absorbing efficiency when the carbon dioxide absorber shown in FIG. 6 is used. The data was obtained by converting $^{14}C$-toluene having known radioactivity into $^{14}CO_2$ by using the oxidation furnace, passing $^{14}CO_2$ through a pair of series connected carbon dioxide absorbers each shown in FIG. 6 and measuring the radioactivity of the absorbed $^{14}CO_2$. It was found that $^{14}CO_2$ was not absorbed in the second absorber. The absorbing efficiency and capacity of $CO_2$ are directly related to the gas flow velocity and the amount of $CO_2$, the slower the velocity providing the higher the efficiency.

As one example of the application of the present invention described as above, a study of metabolism of medicines labelled with $^3H$ and/or $^{14}CO_2$ given to an animal body. It is usual in this study that the respiration of the animal is tested. Heretofore, for example, medicines labelled with $^{14}C$, a whole amount of a radioactivity included in the respiration and a time variation thereof, after the medicines are given to the animal, are measured. Heretofore, it has been also considered that when a cold-trap is used to absorb the water content of the respiration, an error may be introduced into the result of the measurement because $^{14}CO_2$ will resolve itself into the absorbed water. Therefore, it has been usual in the past to collect carbon dioxide by passing the respiration directly through monoethanol amine for a sufficient long time and then to measure a portion of monoethanol amine by a liquid scintillation counting method to thereby determine the amount of the radioactivity thereof.

On the other hand, in the conventional method in which the respiration of the animal is firstly passed through a cold-trap, it has been considered that compounds other than carbon dioxide which include significant amount of radioactivity may be included in the animal respiration and these compounds may also be trapped by the cold-trap, i.e., that the animal respiration may contain various metabolic substances other than carbon dioxide and these substances may be also trapped by the cold-trap. Therefore, it has been usual consideration that it is impossible to use a desiccating means and thus the use of $^3H$ as a label becomes impossible.

The present invention can be effectively applied to an animal respiration collecting device in which both of $^3H$ and $^{14}C$ can be used as labels of medicines, an ordinary exhaust pump can be used in lieu of the aspirator and the sole use of monoethanol amine as a carbon dioxide absorbent. Therefore, the concentration of carbon dioxide available for radioactive measurement becomes very high in comparison with the conventional device and the measuring sensitivity is much improved.

Figure 8:
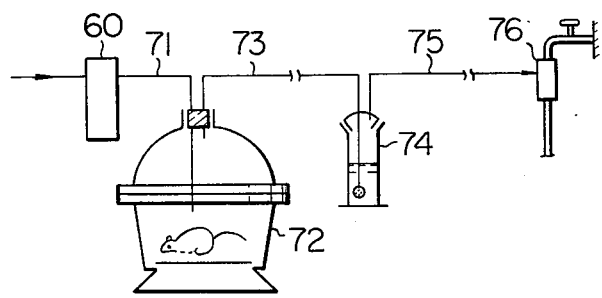
FIG. 8 illustrates schematically an example of the conventional apparatus for collecting carbon dioxide in respiration of small size animal to which carbon-14 labelled medicines are given.

FIG. 8 shows an example of the conventional device of this kind to clarify the features of the present device for comparison. In FIG. 8, fresh air is supplied to a container 72 in which a small size animal such as mouse or rat is enclosed, through a flow meter 60 and a pipe 71, and a respiration of the animal is sent through a pipe 73 to a carbon dioxide collecting jar 74. The collecting jar 74 is filled with monoethanol amine-alcohol or water solution (about 200 ml) and carbon dioxide of the respiration is collected thereby. The remainder of the respiration is exhausted through a pipe 75 by an aspirator 76.

Figure 9:
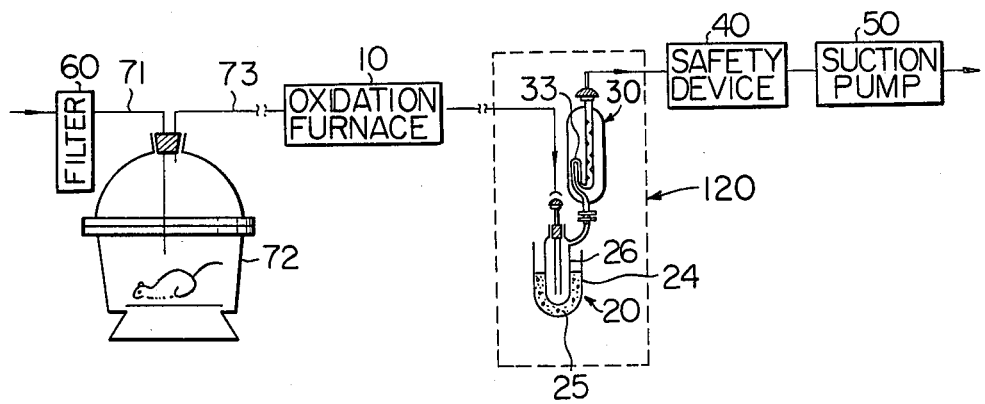
FIG. 9 illustrates, partially in block form, an embodiment of the present invention when applied to an analysis of metabolism of tritium and carbon-14 labelled medicines in a small size animal.

In the apparatus of the present invention shown in FIG. 9, the pipe 73 is connected to an oxidation furnace such as copper oxide burning tube 10 through which the substances containing H and/or C in respiration are converted to $CO_2$ and $H_2O$ as mentioned previously.

$CO_2$ and $H_2O$ are sent to a collecting portion 120. The collecting portion 120 comprises a cold-trap 20 and a carbon dioxide trap 30. The respiration converted enters firstly the cold-trap 20. The cold-trap comprises an outer container 24 containing a coolant 25 such as dry-ice and an inner container 26 immersed in the coolant, $H_2O$ and $CO_2$ are fed through a member having an opening to the lower portion of the inner container 26 and $H_2O$ is trapped therein, and the remainder passes through an outlet port of the inner container 26 and enters the carbon dioxide collecting device 30. It has been found that, in the cold-trap, the undesirable tripping of a substantial amount of carbon dioxide, which has been generally agreed by those skilled in the art, does not occur practically and only water is trapped.

The carbon dioxide trap 30 comprises a syphon portion 33 and a body portion and the carbon dioxide left the cold-tap 20 enters the syphon portion 33 and then the body portion as mentioned previously.

The residual portion of the gas after carbon dioxide was absorbed by the $CO_2$ trap is passed through the safety device 40 containing, for example, activated carbon, molecular sieve or soda lime to prevent any radioactive materials from being exhausted. The gas flow in this system is given by a conventional suction pump 50.

$^3H_2O$ and $^{14}CO_2$ collected in the cold trap 20 and the carbon dioxide trap 30 are suitably recovered respectively and then the radioactivities thereof are measured by the liquid scintillation counting method, respectively.

Figure 10:
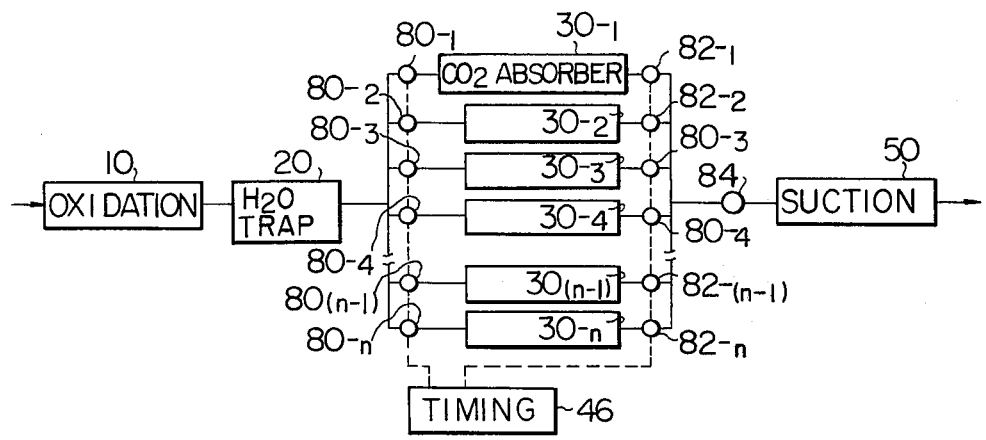
FIG. 10 is another embodiment of the present invention when applied to a continuous analysis of metabolism of carbon-14 labelled medicines in an animal body.

FIG. 10 shows another embodiment of the present invention in which tritium and/or carbon 14 in respiration of the small size animal is continuously measured. That is, the metabolism is a function of time and therefore, in order to analize the metabolism in detail, the change thereof with time must be known. However, in the conventional device, although not always impossible, it is very difficult to measure the variation on time and in the measurement itself requires very great skill and very careful operations including temporal removals of the gas collecting device from the system and, for this reason, not only the contamination problem occurs but also the data obtained becomes intermittent.

The above disadvantages are common for the preceding embodiment.

The object of this embodiment is to provide a continuous respiration collecting device which is simple in construction, capable of continuously collecting animal respiration easily and has all of the advantages of the preceding embodiment. The apparatus shown in FIG. 10 is suitable to collect $^{14}CO_2$, in which, the animal respiration is passed through the oxidation furnace 10 through which it is converted into $H_2O$ and $^{14}CO_2$. This conversion is performed for components other than $CO_2$, containing $^{14}C$. By doing so, such compounds are converted into $CO_2$ and errors which would otherwise occur in $^{14}CO_2$ collection in the subsequent stages are eliminated.

The mixture gas derived from the oxidation furnace 10 enters water trap 20 such as cold-trap and is dehydrated thereby.

The cold-trap 20 is connected to inlet ports of a plurality of parallel arranged carbon dioxide traps 30 through respective anti-diffusion valves 80 such as normally closed switch cocks or, preferably, normally closed electromagnetic valves and output ports if the traps 30 are connected to a common suction pump 50 through respective check valves 82, preferably, of electromagnetic type. The carbon dioxide trap is this embodiment is the same as that used in the preceding embodiment. The valves 80 are for preventing gas from entering into the cold traps other than the desired one and the valves 82 are for preventing gas flown out from the desired $CO_2$ trap from entering back into other $CO_2$ traps. The valves 80 and the valves 82 are controlled automatically by an automatic timing device 46 to be sequentially opened and closed such that only one of the traps is available at one of a series of collecting intervals. The construction of the automatic timing device 46 and the constructions of the valves 80 and 82 to be controlled thereby are obvious for those skilled in the art and therefore the details thereof are omitted. Further, the valves 80 may be omitted, if necessary.

When one of the valves 80, i.e., 80-1 and one of the check valves, i.e., 82-1 are opened by the timing device 46, the gas from the cold-trap 20 passes through the valve 80-1 and enters a carbon dioxide trap 30-1 in which the carbon dioxide content thereof is absorbed in monoethanol amine and residual content is exhausted by the suction pump. The needle valve 84 is to prevent an over-suction by the pump 50. Further, it may be possible to provide a safety device 40 similar to the device in the preceding embodiment.

Figure 11:
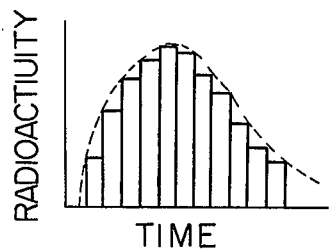
FIG. 11 shows an explanatory graph of data obtainable by the apparatus in FIG. 10.

After a predetermined time interval the valve 80-1 and the valve 82-1 are closed by the timing device 46. At the same time, the valve 80-2 and the check valve 82-2 are opened by the same to trap the carbon dioxide content in the trap 30-2, and so on. In this manner, the carbon dioxide is continuously collected in the traps 30-1 to 30-$n$ sequentially, the amount of $CO_2$ in each trap 30 showing the time variation. By measuring the radioactivity of $^{14}CO_2$ trapped in the traps 30-1 to 30-$n$, a data such as shown in FIG. 11 is obtainable, the envelope of which represents the time variation of the object in the animal respiration.

Figure 12:
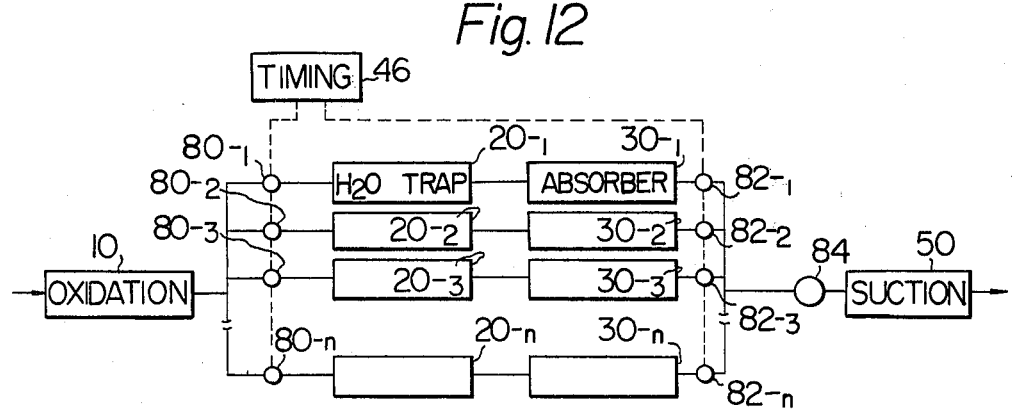
FIG. 12 is another embodiment of the present invention when applied to a continuous analysis of metabolism of tritium and carbon-14 labelled medicines in an animal body.

FIG. 12 shows another embodiment which is adapted to collect both of $^3H$ and $^{14}C$ for study of metabolism of medicines containing $^3H$ and $^{14}C$ as labels. The difference between this embodiment and the last embodiment is that the former includes a cold-trap 20 in each of the parallel flow lines.

Although there is no limitation in the number of the parallel lines it will be clear that the larger the number with the shorter interval provides the more precise the analysis. The cold-trap and the carbon dioxide trap used therein may be the same as those used in the preceding embodiments and the constructions of the various valve means may be arbitrarily selected.

What is claimed is:
1. A radioactive measuring apparatus for tritium and carbon-14 contained in a flowing gas sample, comprising
an oxidation means having an inlet port and an outlet port for continuously converting compounds containing hydrogen and carbon into water and carbon dioxide;
at least one water collecting means comprising a cold-trap having an inlet port connected to said outlet port of said oxidation means and an outlet port, for collecting the water content of the oxidized gas;
at least one carbon dioxide collecting means having an inlet port connected to said outlet port of said water collecting means and an outlet port and containing monoethanol amine to absorb carbon dioxide in the output gas from said water collecting means wherein said carbon dioxide collecting means comprises a syphon and an upstanding body portion defined by portion and cylindrical wall with an inlet port at the bottom thereof and an outlet port at an upper end thereof, one end of said syphon portion being connected to said outlet port of said cold-trap and the other end of said syphon portion being connected to said inlet port of said upstanding body portion, the inner surface of said wall being provided with a plurality of protrusions, whereby, when monoethanol amine is supplied from said outlet port of said upstanding body portion into the interior of said body portion up to a level corresponding to the height of said syphon portion and then the gas containing carbon dioxide is fed through said syphon to said inlet port of said body portion, the gas rises as bubbles through monoethanol amine, each of the bubbles is subdivided by said protrusions on the way of the rising thereof and broken at around the level of monoethanol amine to facilitate the dissolution of carbon dioxide into monoethanol amine;
a suction pump means having an inlet port connected to said outlet port of said carbon dioxide collecting means for producing a flow of the gas through the series connection of said oxidation means, said water collecting means and said carbon dioxide collecting means; and means for measuring radioactivities of tritium and/or carbon-14 contained in the water and/or carbon dioxide collected by said water collecting means and said carbon dioxide collecting means.

2. A radioactive measuring apparatus for tritium and carbon-14 contained in a flowing gas sample, comprising an oxidation means having an inlet port and an output port for continuously converting compounds containing hydrogen and carbon into water and carbon dioxide;

at least one water collecting means comprising a cold-trap having an inlet port connected to said outlet port of said oxidation means and an outlet port, for collecting the water content of the oxidized gas;

at least one carbon dioxide collecting means having an inlet port connected to said outlet port of said water collecting means and an outlet port and containing monoethanol amine to absorb carbon dioxide in the output gas from said water collecting means wherein a plurality of said carbon dioxide collecting means are provided in parallel with each other with a normally closed check valve means disposed in the down stream side of each carbon dioxide collecting means, the inlet ports of said carbon dioxide collecting means being connected commonly to the outlet port of said cold-trap, wherein outlet ports of said check valves are connected commonly to a needle valve for preventing an oversuction of said suction pump and wherin an automatic timing means is provided for controlling said check valves to selectively open one of said check valves sequentially to thereby enable a continuous detection of radioactivity of carbon-14 as a function of time;

a suction pump means having an inlet port connected to said outlet port of said carbon dioxide collecting means for producing a flow of the gas through the series connection of said oxidation means, said water collecting means and said carbon dioxide collecting means; and means for measuring radioactivities of tritium and/or carbon-14 contained in the water and/or carbon dioxide collected by said water collecting means and said carbon dioxide collecting means.

3. A radioactive measuring apparatus according to claim 2, wherein a normally closed diffusion proof valve is provided in the upstream side of each carbon dioxide collecting means, the inlet ports of said diffusion proof valves being connected commonly to the outlet port of said water collecting means and wherein said diffusion proof valves are controlled by said automatic timing means.

4. A radioactive measuring apparatus according to claim 2, wherein a plurality of said water collecting means are provided in parallel with each other, said water collecting means being connected in series with said carbon dioxide collecting means respectively, the inlet ports of said water collecting means being connected commonly to the outlet port of said oxidation means.

* * * * *